United States Patent
Orr et al.

(10) Patent No.: US 6,217,524 B1
(45) Date of Patent: Apr. 17, 2001

(54) METHOD OF CONTINUOUSLY, NON-INVASIVELY MONITORING PULMONARY CAPILLARY BLOOD FLOW AND CARDIAC OUTPUT

(75) Inventors: Joseph A. Orr, Park City, UT (US); Michael B. Jaffe, Cheshire, CT (US); Kai Kück, Hamburg (DE); Dinesh G. Haryadi, Bangalore (IN)

(73) Assignee: NTC Technology Inc., Wilmington, DE (US)

( * ) Notice: Subject to any disclaimer, the term of this patent is extended or adjusted under 35 U.S.C. 154(b) by 0 days.

(21) Appl. No.: 09/150,446

(22) Filed: Sep. 9, 1998

(51) Int. Cl.$^7$ ................................. A61B 5/02; A61B 5/08
(52) U.S. Cl. ........................ 600/504; 600/500; 600/532; 128/204.12
(58) Field of Search ..................................... 600/500–504, 600/526, 528–538, 300, 301, 481–486; 128/204.12–204.23

(56) References Cited

U.S. PATENT DOCUMENTS

| | | |
|---|---|---|
| 4,221,224 | 9/1980 | Clark . |
| 4,463,764 | 8/1984 | Anderson et al. . |
| 5,060,656 | 10/1991 | Howard . |
| 5,069,220 | 12/1991 | Casparie et al. . |
| 5,117,674 | 6/1992 | Howard . |
| 5,178,155 | 1/1993 | Mault . |
| 5,285,794 | 2/1994 | Lynch . |
| 5,299,579 | 4/1994 | Gedeon et al. . |
| 5,402,796 | 4/1995 | Packer et al. . |
| 5,632,281 | 5/1997 | Rayburn . |
| 5,836,300 | * 11/1998 | Mault ................................... 600/532 |
| 5,971,934 | * 10/1999 | Scherer et al. ...................... 600/526 |

FOREIGN PATENT DOCUMENTS

WO 98/12963   4/1998 (WO) .

OTHER PUBLICATIONS

H. Blomquist et al., *A Non–Invasive Technique for Measurement of Lung Perfusion*, Intensive Care Medicine 1986; 12:172.

R.J. Bosman et al, *Non–Invasive Pulimonary Blood Flow Measurement by Means of $CO_2$ Analysis Of Expiratory Gases*, Intensive Care Medicine 1991, 17:98–102.

(List continued on next page.)

*Primary Examiner*—Cary O'Connor
*Assistant Examiner*—M. Astorino
(74) *Attorney, Agent, or Firm*—TraskBritt (57) ABSTRACT

A method of continuously, non-invasively determining the cardiac output of a patient. The method includes intermittently measuring the cardiac output, the volume of carbon dioxide exhaled by the patient per breath, and determining the arterial-venous gradient of the patient or a similar substantially constant value by dividing the volume of carbon dioxide exhaled by the measured cardiac output. The arterial-venous gradient or similar substantially constant value may then be employed to determine the cardiac output of the patient on a breath-by-breath basis. The carbon dioxide elimination, which is non-invasively measured as the volume of carbon dioxide exhaled by the patient per breath, is divided by the arterial-venous gradient or the substantially constant value to determine the cardiac output. The method may also include generating a signal to compensate for any non-metabolic changes in the carbon dioxide elimination, arterial-venous gradient, or other respiratory or blood gas profile measurements that may be caused by a change in ventilation or breathing of the patient. The compensatory signal may be employed to modify one or more of the respiratory or blood gas profile measurements in order to facilitate the accurate determination of cardiac output during or after changes in ventilation or breathing.

56 Claims, 5 Drawing Sheets

OTHER PUBLICATIONS

A. Gedeon, *Non–Invasive Pulmonary Blood Flow for Optimal Peep*, ICOR AB, Ulvsundavagen 178 B, S–161 30 Bromma, Sweden, pp. 49–58.

Capek, J.M., *Noninvasive Measurement of Cardiac Output Using Partial $CO_2$ Rebreathing* [Dissertation], Rensselaer Polytechnic Institute (1988) 28:351 p. (due to large number of pages, only table of contents and abstract have been copied).

Capek, J.M., et al., *Noninvasive Measurement of Cardiac Output Using Partial $CO_2$ Rebreathing*, IEEE Trans. Biomed. Eng. (1988) 35(9):653–61.

Davies, Gerald G., et al., *Continuous Fick cardiac output compared to thermodilution cardiac output*, Critical Care Medicine (1986) 14(10):881–85.

Elliot, C. Gregory, et al., *Complications of Pulmonary Artery Catheterization in the Care of Critically Ill Patients*, Chest (1979) 76:647–52.

Fick, A., *über die Messung des Blutquantums in den Herzventrikeln*, Sitzungsbericht der Physikalisch–Medizinischen Gesellschaft zu Würzburg (1870) 36 (2 pages).

Gama de Abreu, Marcelo, et al., *Measurement of Pulmonary Capillary Blood Flow for Trending Mixed Venous Blood Oxygen Saturation and Oxygen Delivery*, Crit. Care Med (1998) vol. 26, No. 1 (Suppl), A106, Abstract #238 (1 page).

Gama de Abreu, Marcelo, et al., *Is the Partial $CO_2$ Rebreathing Technique a Useful Tool for Trending Pulmonary Capillary Blood Flow During Adjustments of Peep?*, Crit. Care Med (1998) vol. 26, No. 1 (Suppl), A106, Abstract #237, (1 page).

Gama de Abreu, et al., *Partial carbon dioxide rebreathing: A reliable technique for noninvasive measurement of non-shunted pulmonary capillary blood flow*, Crit. Care Med (1997) 25(4):675–83.

Gedeon, A., et al., *Noninvasive Cardiac Output Determined with a New Method Based on Gas Exchange Measurements and Carbon Dioxide Rebreathing: A Study in Animals/Pigs*, J. Clin. Monit. (1992) 8(4):267–78.

Gedeon, A., et al., *A new method for noninvasive bedside determination of pulmonary blood flow*, Med. & Biol. Eng. & Comput. (1980) 18:411–418.

Guyton, A.E., et al., *Measurement of cardiac output by the direct Fick method*, In: Cardiac output and its regulation, W.B. Saunders Company (1973) 21–39.

Kyoku, I., et al. *Measurement of cardiac output by Fick method using $CO_2$ analyzer Servo*, Kyobu Geka. Japanese Journal of Thoracic Surgery (1988) 41(12):966–70.

Lynch, J., et al., *Comparison of a modified Fick method with thermodilution for determining cardiac output in critically ill patients on mechanical ventilation*, Intensive Care Med. (1990) 16:248–51.

Mahutte, C. Kees, et al., *Relationship of Thermodilution Cardiac Output to Metabolic Measurements and Mixed Venous Oxygen Saturation*, Chest (1993) 104(4):1236–42.

Miller, D.M., et al., *A Simple Method for the Continuous Noninvasive Estimate of Cardiac Output Using the Maxima Breathing System. A Pilot Study*, Anaesth. Intens. Care (1997) 25(1):23–28.

Österlund, B., et al., *A new method of using gas exchange measurements for the noninvasive determination of cardiac output: clinical experiences in adults following cardiac surgery*, Acta Anaesthesiol Scand (1995) 39:727–32.

Sackner, Marvin A., *Measurement of cardiac output by alveolar gas exchange*, Handbook of Physiology–The Respiratory System IV, Chapter 13, 233–55.

Spalding, H. K., et al., *Carbon Dioxide ($CO_2$) Elimination Rate Accurately Predicts Cardiac Output*, Anesthesiology (1997) 87(3A) (1 page).

Sprung, Charles L., et al., *Ventricular Arrhythmias During Swan–Ganz Catherization of the Critically Ill*, Chest (1981) 79:413–15.

Taskar, V., et al., *Dynamics of Carbon Dioxide Elimination Following Ventilator Resetting*, Chest (1995) 108:196–202.

Winkler, Tilo, et al., *Pulmonary Capillary Blood Flow by Partial $CO_2$ Rebreathing: A Simulation Study Using a Bicompartmental Model of Gas Exchange*, Crit Care Med (1998) vol. 26, No. 1 (Suppl), A105, Abstract #234 (1 page).

Mahutte, C.K., et al., "Cardiac Output from Cardon Dioxide Production and Arterial and Venous Oximetry," *Critical Care Medicine*, vol. 19, No. 10, Oct. 1991, pp. 1270–1277.

Mahutte, C.K., et al., "Oxygen Fick and Modified Carbon Dioxide Fick Cardiac Outputs," *Critical Care Medicine*, vol. 22, No. 1, Jan. 1994, pp. 86–95.

Jaffe, M.B., Dissertation: A Modified Fick Method for the Estimation of Cardiac Output, University of Southern California, May 1994.

* cited by examiner

METHOD OF CONTINUOUSLY, NON-INVASIVELY MONITORING PULMONARY CAPILLARY BLOOD FLOW AND CARDIAC OUTPUT

BACKGROUND OF THE INVENTION

1. Field of the Invention

The present invention relates to methods of monitoring the cardiac output or pulmonary capillary blood flow of a patient. More specifically, the present invention relates to methods of continuously monitoring the cardiac output or pulmonary capillary blood flow of a patient during each breath or respiratory cycle, flow, and, particularly, to methods of continuously, non-invasively determining cardiac output or pulmonary capillary blood flow. The present invention also relates to methods of monitoring the cardiac output or pulmonary capillary blood flow of a patient during both stable ventilation or breathing and during or following changes in ventilation or breathing.

2. Background of Related Art

Conventionally, cardiac output has been measured both intermittently and continuously. Intermittent techniques of measuring cardiac output include invasive and non-invasive techniques.

Indicator dilution, an exemplary invasive, typically intermittent technique for measuring cardiac output, includes introducing a predetermined amount of an indicator into the bloodstream through the heart of a patient and analyzing blood downstream from the point of introduction to obtain a time vs. dilution curve. Thermodilution, in which room temperature or colder saline solution, which may be referred to as "cold" saline, is employed as the indicator, is a widely employed type of indicator dilution. Typically, the cold saline is introduced into the right heart bloodstream of a patient through a thermodilution catheter, which includes a thermistor at an end thereof. The thermistor is employed to measure the temperature of the blood after it has passed through the right heart, or downstream from the point at which the cold saline is introduced. A thermodilution curve is then generated from the data, from which the cardiac output of the patient may be derived. Thermodilution and other indicator dilution techniques are, however, somewhat undesirable due to the potential for harm to the patient that is associated with inserting and maintaining such catheters in place.

One of the less invasive conventional techniques for measuring the cardiac output of a patient employs the Fick principle: the rate of uptake of a substance by or release of a substance from blood at the lung is equal to the blood flow past the lung and the content difference of the substance at each side of the lung.

The Fick principle may be represented in terms of oxygen ($O_2$) by the following formula:

$$Q_t = VO_2/(CaO_2 - CvO_2),$$

where $Q_t$ is the cardiac output, or blood flow, of the patient, $VO_2$ is the net volume of oxygen consumed by the patient per unit of time, $CaO_2$ is the content of $O_2$ in the arterial, or oxygenated, blood of the patient, and $CvO_2$ is the content of $O_2$ in the venous, or de-oxygenated, blood of the patient. The oxygen Fick principle may be employed in calculating the cardiac output of a patient either intermittently or continuously.

An exemplary, so-called "non-invasive", method of determining the cardiac output of a patient by monitoring $VO_2$ is disclosed in Davies et al., Continuous Fick cardiac output compared to thermodilution cardiac output, *Crit. Care Med.* 1986; 14:881–885 ("Davies"). The method of Davies includes continually measuring the $O_2$ fraction of samples of gas inspired and expired by a patient, the oxygen saturation ($SvO_2$) of the patient's venous blood, and oxygen saturation ($SaO_2$) of the patient's arterial blood. The $O_2$ measurements are made by a metabolic gas monitor, and $VO_2$ calculated from these measurements. $SaO_2$ is measured by pulse oximetry. $SvO_2$ may be directly measured by a pulmonary artery ("PA") catheter equipped to measure oxygen saturation. Each of these values is then incorporated into the oxygen Fick equation to determine the cardiac output of the patient. Although the method of Davies may be employed to intermittently or continuously determine the cardiac output of a patient, it is somewhat undesirable from the standpoint that accurate $VO_2$ measurements are typically difficult to obtain, especially when the patient requires an elevated fraction of inspired oxygen ($FiO_2$). Moreover, since the method disclosed in Davies requires continual measurement of $SvO_2$ with a pulmonary artery catheter, it is, in actuality, an invasive technique.

Due in part to the ease with which the carbon dioxide elimination ($VCO_2$) of a patient may be accurately measured, $VCO_2$ measurements are widely employed in methods of non-invasively determining the cardiac output of a patient. Since the respiratory quotient (RQ) is the ratio of carbon dioxide elimination to the amount of oxygen inhaled, $VCO_2$ may be substituted for $VO_2$ according to the following exemplary equation:

$$VO_2 = VCO_2/RQ.$$

An exemplary method of continuously measuring the cardiac output of a patient in terms of $CO_2$ is disclosed in U.S. Pat. No. 4,949,724 ("the '724 patent"), which issued to Mahutte et al. on Aug. 21, 1990. The method of the '724 patent employs the following form of the Fick equation to determine the cardiac output of a patient:

$$Q_t = VCO_2/(Hgb \cdot RQ \cdot (SaO_2 - SvO_2)),$$

where $VCO_2/(Hgb \cdot RQ \cdot (SaO_2 - SvO_2))$ has been substituted for $VO_2/(CaO_2 - CvO_2)$ and Hgb is the concentration of hemoglobin in the blood (typically about 13.4 g/dl). A constant, k, may be employed to replace either Hgb or $Hgb \cdot RQ$.

According to the method of the '724 patent, an initial cardiac output measurement is made by thermodilution techniques. Thereafter, k is calculated. Subsequently, a $CO_2$ flowmeter and monitor are employed to measure $VCO_2$, $SvO_2$ is measured with a catheter and oximetry processor, and $SaO_2$ is measured by a pulse oximeter. The cardiac output of the patient may be continuously calculated as described above. The method of continuously measuring cardiac output of the '724 patent is, however, somewhat undesirable as the use of a catheter to initially determine cardiac output and to continuously measure $SvO_2$ is invasive and may thus create additional health risks for the patient.

Alternatively, a modification of the Fick principle, which is based on the exchange of carbon dioxide ($CO_2$) in the lungs of a patient, has been employed to calculate the cardiac output of the patient. The carbon dioxide Fick equation, which represents the Fick principle in terms of $CO_2$ production and exchange, follows:

$$Q_1 = VCO_2/(CvCO_2 - CaCO_2),$$

where $CvCO_2$ is the content of $CO_2$ in the venous blood of the patient and $CaCO_2$ is the content of $CO_2$ in the arterial blood of the patient. The difference between $CvCO_2$ and $CaCO_2$ is typically referred to as the arterial-venous carbon dioxide gradient, "AV $CO_2$ gradient", or simply "AV gradient".

The carbon dioxide Fick equation has been employed to non-invasively determine the cardiac output of a patient on an intermittent basis. The carbon dioxide elimination of the patient may be non-invasively measured as the difference per breath between the volume of carbon dioxide inhaled during inspiration and the volume of carbon dioxide exhaled during expiration. The volume of carbon dioxide inhaled and exhaled may each be corrected for any deadspace. The partial pressure of end-tidal carbon dioxide ($PetCO_2$), after correcting for any deadspace, is typically assumed to be approximately equal to the partial pressure of carbon dioxide in the alveoli ($PACO_2$) of the patient or, if there is no intrapulmonary shunt, the partial pressure of carbon dioxide in the arterial blood of the patient ($PaCO_2$). A re-breathing process is typically employed either to non-invasively estimate the carbon dioxide content of mixed venous blood (in total re-breathing) or to obviate the need to know the carbon dioxide content of the mixed venous blood (by partial re-breathing). Re-breathing processes typically include the inhalation of a gas mixture which includes carbon dioxide. During re-breathing, the $CO_2$ production of the patient is less than during normal breathing. Re-breathing during which the $CO_2$ production decreases to near zero is typically referred to as total re-breathing. Re-breathing that causes some decrease, but not a total cessation of $CO_2$ elimination, is typically referred to as partial re-breathing.

Figure 1:
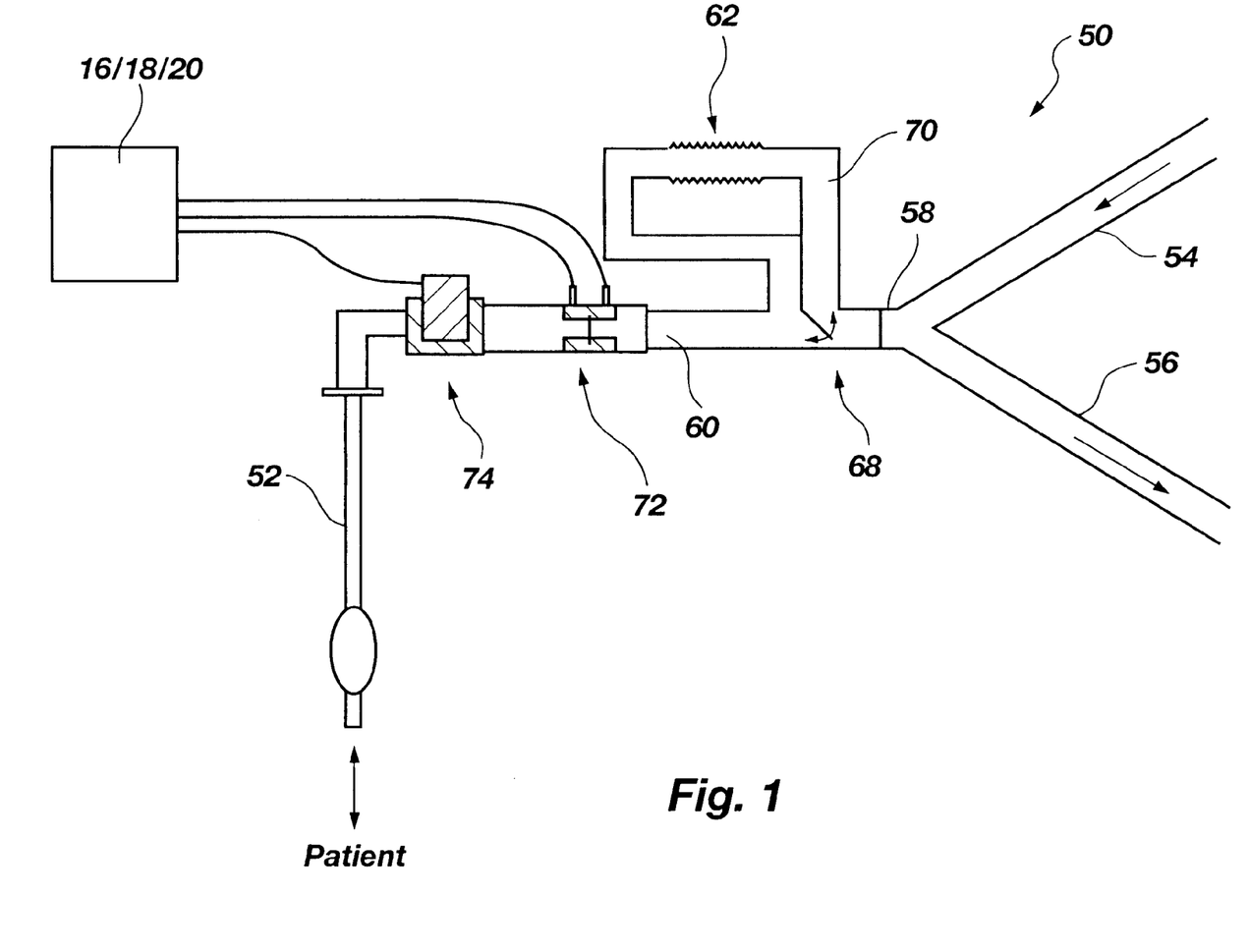
FIG. 1 is a schematic representation of an exemplary re-breathing circuit that may be employed with the methods of the present invention.

Re-breathing is typically conducted with a re-breathing circuit, which causes a patient to inhale a gas mixture that includes carbon dioxide. FIG. 1 schematically illustrates an exemplary re-breathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60, and are exposed to any air that flows through re-breathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to re-breathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During re-breathing, valve 68 is positioned to direct the flow of exhaled and inhaled gases through deadspace 70.

During total re-breathing, the partial pressure of end-tidal carbon dioxide ($PetCO_2$ or $etCO_2$) is typically assumed to be equal to the partial pressure of carbon dioxide in the venous blood ($PvCO_2$) of the patient, as well as to the partial pressures of carbon dioxide in the alveolar blood ($PACO_2$) and in the arterial blood ($PaCO_2$). The partial pressure of carbon dioxide in blood may be converted to the content of carbon dioxide in blood by means of a carbon dioxide dissociation curve.

In partial re-breathing, measurements during normal breathing and subsequent re-breathing are substituted into the carbon dioxide Fick equation. This results in a system of two equations and two unknowns (carbon dioxide content in the mixed venous blood and cardiac output), which can be solved for $Q_1$ without requiring knowledge of the carbon dioxide content in the mixed venous blood.

Alternative differential Fick methods of measuring pulmonary capillary blood flow or cardiac output have also been employed. Such differential Fick methods typically include a brief change of $PetCO_2$ and $VCO_2$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by re-breathing. An exemplary differential Fick method that has been employed, which is disclosed in Gedeon, A. et al. in 18 *Med. & Biol. Eng. & Comput.* 411–418 (1980), employs a period of increased ventilation followed immediately by a period of decreased ventilation.

An exemplary non-invasive breath-by-breath, or continuous, method of estimating cardiac output based on the carbon dioxide Fick equation is disclosed in Miller et al., A Simple Method for the Continuous Noninvasive Estimate of Cardiac Output Using the Maxima Breathing System. A Pilot Study, *Anaesth. Intens. Care* 1997; 25:23–28 ("Miller"). The methods of Miller are conducted on the so-called "Maxima" breathing system, which is a valveless, disposable, universal breathing system that selectively substantially eliminates alveolar gas. Since alveolar gas is eliminated, use of the Maxima breathing system facilitates a series of assumptions which lead to the following form of the carbon dioxide Fick equation:

$$Q_t = VF \cdot FECO_2/(CaCO_2 - CvCO_2),$$

where VF is the flow of fresh gas into the lungs of the patient and $FECO_2$ is the volumetric fraction of carbon dioxide in the expiratory tidal volume of the patient's respiration. In accordance with the method of Miller, VF is adjusted to achieve a substantially constant $FECO_2$ value in the range of 4.0–4.2%. Thus, in order for this method to provide an accurate breath-by-breath estimate of cardiac output, the breathing or ventilation of a patient should be stable. Since the mean $CaCO_2 - CvCO_2$ in patients with normal hemoglobin concentrations is typically assumed to be approximately 4 volumes percent, $FECO_2/(CaCO_2 - CVCO_2)$ is typically about one. Thus, the cardiac output of a patient may be determined in accordance with the method of Miller by determining the flow of fresh gas into the lungs of the patient. Because the method of Miller requires control over the fresh gas flow into the lungs of a patient:, it may not be employed to determine the cardiac output of non-ventilated patients or during or after changes in breathing. Moreover, the method of Miller requires that a particular type of ventilation apparatus be employed to measure the cardiac output of a patient.

Alternative methods disclosed in Miller that may be employed to measure the cardiac output of a patient also require a measurement of the concentration of hemoglobin in the blood of the patient and/or estimation of $CO_2$ diffused in the plasma (i.e., not carried by hemoglobin). These alternative methods are somewhat undesirable in that measurement of hemoglobin concentration is typically invasive.

Thus, there is a need for a non-invasive method of continuously determining the cardiac output or pulmonary capillary blood flow of a patient that may be conducted during both normal, stable breathing and during or following changes in breathing or ventilation. There is also a need for a method of non-invasively, continuously determining the cardiac output or pulmonary capillary blood flow of both ventilated and non-ventilated patients.

SUMMARY OF THE INVENTION

The method of non-invasively measuring the cardiac output or pulmonary capillary blood flow of a patient on a breath-by-breath basis, or "continuously", according to the present invention addresses the foregoing needs.

A first embodiment of the method includes measuring the cardiac output or pulmonary capillary blood flow of a patient by an intermittent method, such as by known invasive (e.g., indicator dilution) or non-invasive (e.g., partial or total re-breathing or other non-invasive, differential Fick) techniques, in order to obtain an accurate cardiac output or pulmonary capillary blood flow measurement. Preferably, the intermittent cardiac output or pulmonary capillary blood flow measurement is corrected for the presence of any deadspace or intrapulmonary shunt.

The carbon dioxide elimination of the patient is non-invasively determined by measuring the net volume of carbon dioxide exhaled by the patient per breath. The carbon dioxide elimination is then divided by the intermittently measured cardiac output or pulmonary capillary blood flow value to determine a scaling value, such as the arterial-venous carbon dioxide gradient of the patient.

The scaling value preferably includes at least one component that remains substantially constant over short periods of time, such as one, five, or ten minutes or more. The portion of the scaling value that remains substantially constant is referred to as a scaling factor. Accordingly, the scaling factor may comprise a portion of the scaling value or the entire scaling value.

The arterial-venous carbon dioxide gradient of a patient typically remains substantially constant over periods of time, as carbon dioxide stores in the blood and other tissues of a patient remain substantially unchanged. Accordingly, the arterial-venous gradient may be employed as the scaling value with a per breath measurement of the carbon dioxide elimination of the patient in order to determine the cardiac output of the patient on a breath-by-breath basis. The carbon dioxide elimination, which may be measured in a single breath or as a per breath average of several breaths, is divided by the intermittently determined arterial-venous carbon dioxide gradient to determine cardiac output or pulmonary capillary blood flow. The cardiac output or pulmonary capillary blood flow value may also be modified or corrected by an offset constant.

The intermittent cardiac output or pulmonary capillary blood flow measurement may be repeated periodically or as needed and, preferably, prior to a significant change in the carbon dioxide stores of the blood or other tissues of the patient. The size and time constant of the carbon dioxide stores may be estimated by known processes, which include, but are not limited to, determining the amount of the patient's anatomic deadspace, body weight, height, age, etc. When the time constant of the carbon dioxide stores is estimated, the frequency with which the intermittent cardiac output or pulmonary capillary blood flow measurement should be repeated may be estimated and optimized.

Typically, changes in ventilation or breathing non-metabolically alter one or more respiratory profile parameters, such as non-invasively measured carbon dioxide elimination and end tidal partial pressure of carbon dioxide. Thus, the method of the present invention also preferably includes generating a compensatory signal if the ventilation or breathing of the patient changes. Once a ventilation or breathing instability or a non-metabolic change in a respiratory profile parameter is detected, a compensatory signal may be generated by determining the magnitude of the non-metabolic change and the amount of time since the onset of the non-metabolic change. Various other factors may also be considered in generating the compensatory signal, including, without limitation, the type of breathing instability and the condition of the patient's lungs. The compensatory signal may then be employed to modify one or more of the parameters that are used to determine cardiac output on a breath-by-breath basis.

A second embodiment of the method of the present invention, which is similar to the first embodiment, includes continuously measuring one or more blood profile parameters of the patient rather than determining the arterial-venous gradient from intermittent cardiac output or pulmonary capillary blood flow measurements. Exemplary blood profile parameters that may be continuously measured include, but are not limited to the end capillary oxygen content of the patient's blood, the oxygen content of the venous blood of the patient, the oxygen or carbon dioxide saturation of the arterial or venous blood of the patient, or the partial pressure of oxygen or carbon dioxide of the arterial or venous blood of the patient. Preferably, the continuously measured blood gas parameter is measured by non-invasive means. The measured blood gas parameter may then be employed, as the arterial-venous gradient in the first embodiment, with a per breath carbon dioxide elimination measurement and a constant value or one or more assumed, substantially constant, or continuously measured parameters to determine the cardiac output or pulmonary capillary blood flow of the patient on a breath-by-breath basis. As with the first embodiment, a compensatory signal may be generated to compensate for non-metabolic changes to any of the parameters employed in determining cardiac output.

Alternatively, the scaling factor or the offset constant may be employed to obtain a continuous, non-invasive cardiac output or pulmonary capillary blood flow measurement from the oxygen consumption of a patient.

Other features and advantages of the method of the present invention will become apparent to those in the art through consideration of the ensuing description, the accompanying drawings, and the appended claims.

DETAILED DESCRIPTION OF THE PREFERRED EMBODIMENTS

A preferred embodiment of the method of the present invention includes intermittently measuring the cardiac output of a patient and determining a constant value that may be employed to calculate the cardiac output of the patient on a breath-by-breath basis. The method also includes non-invasively measuring a respiratory profile parameter of the patient, such as $VCO_2$, on a breath-by-breath basis. The respiratory profile parameter and the constant value are then employed to calculate the cardiac output of the patient until another intermittent measurement may be made. Preferably, the present invention also includes a method of modifying the constant value during or following changes in ventilation or breathing.

Intermittent Cardiac Output Measurement

Due to the technical difficulty of measuring the amount of oxygen ($O_2$) consumed by a patient ($VO_2$), especially in patients who require an elevated fraction of inspired oxygen, cardiac output ($Q_t$) is preferably measured in terms of the amount of carbon dioxide ($CO_2$) excreted into the lungs of the patient, which is typically measured in terms of $CO_2$ elimination ($VCO_2$). The Fick equation for non-invasive measurement of cardiac output, in terms of $CO_2$, and which is generally accepted in the art as a standard for the non-invasive measurement of cardiac output, is:

$$Q_t = VCO_2/(CvCO_2 - CaCO_2).$$

Measuring Respiratory, Blood and Blood Gas Profile Parameters

Figure 3:
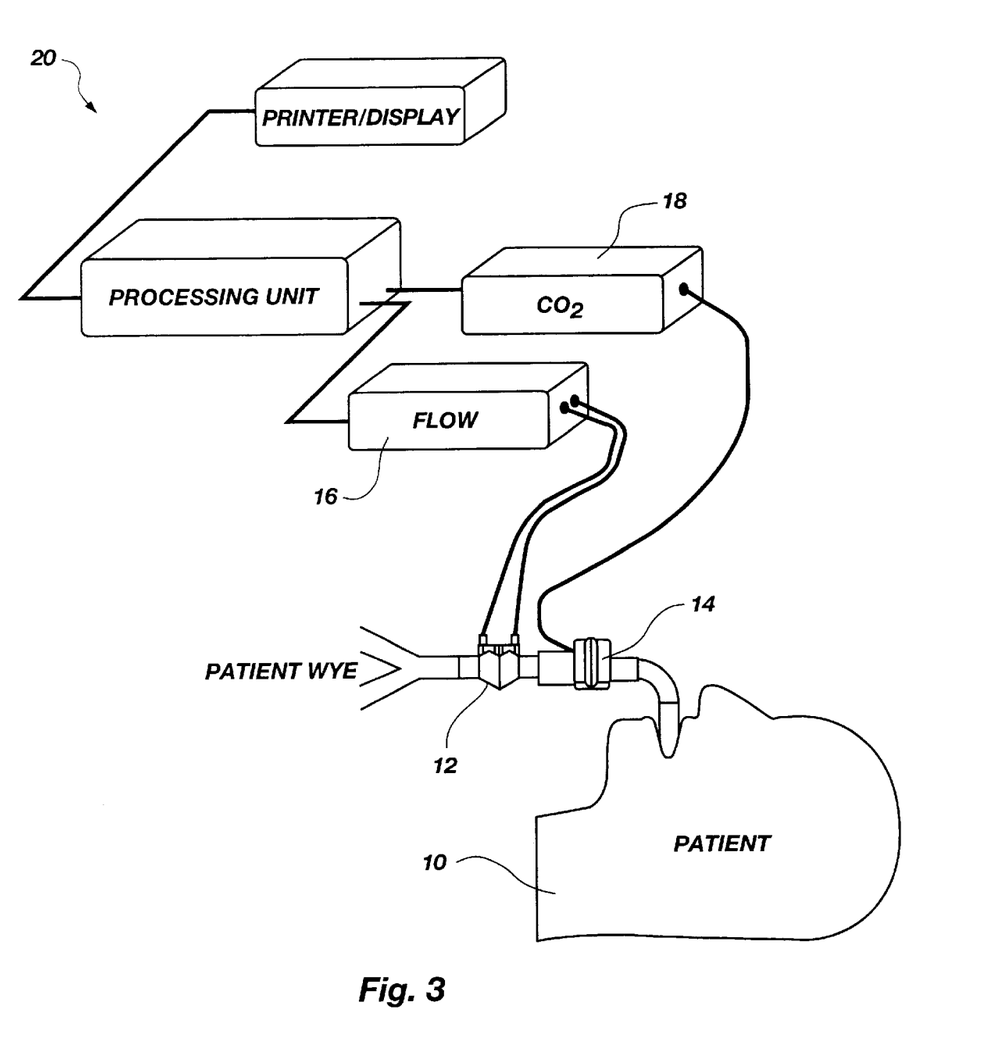
FIG. 3 is a schematic representation which illustrates the various componentry that may be utilized to measure respiratory profile parameters that are employed in the methods of the present invention.

With reference to FIG. 3, a preferred embodiment of the method of the present invention includes non-invasively measuring the flow rates and $CO_2$ fraction of gas mixtures that are inhaled and exhaled by a patient 10 over the course of the patient's breathing during known re-breathing techniques. A flow sensor 12 of a known type, such as the differential-pressure type respiratory flow sensors manufactured by Novametrix Medical Systems Inc. ("Novametrix") of Wallingford, Conn. (e.g, the Pediatric/Adult Flow Sensor (Catalog No. 6717) or the Neonatal Flow Sensor (Catalog No. 6718)), which may be operatively attached to a ventilation apparatus (not shown), as well as respiratory flow sensors based on other operating principles and manufactured or marketed by Novametrix or others, may be employed to measure the flow rates of the breathing of patient 10. A $CO_2$ sensor 14, such as the CAPNOSTAT® $CO_2$ sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053)), which are manufactured by Novametrix, as well as other main stream and side stream $CO_2$ sensors manufactured or marketed by Novametrix or others, may be employed to measure the $CO_2$ fraction of gas mixtures that are inhaled and exhaled by patient 10. Flow sensor 12 and $CO_2$ sensor 14 are connected to a flow monitor 16 and a $CO_2$ monitor 18, respectively, each of which may be operatively associated with a computer 20 so that data from the flow and $CO_2$ monitors 16 and 18, representative of the signals from each of flow sensor 12 and $CO_2$ sensor 14, may be detected by computer 20 and processed according to programming (e.g., by software) thereof. Preferably, raw flow and $CO_2$ signals from the flow monitor and $CO_2$ sensor are filtered to remove any significant artifacts. As respiratory flow and $CO_2$ pressure measurements are made, the respiratory flow and $CO_2$ pressure data may be stored by computer 20. Thus, cardiac output may be calculated, in accordance with the carbon dioxide Fick equation or by any other suitable equation known in the art, by computer 20.

Each breath, or breathing cycle, of patient 10 may be delineated, as known in the art, such as by continuously monitoring the flow rate of the breathing of patient 10.

Figure 4:
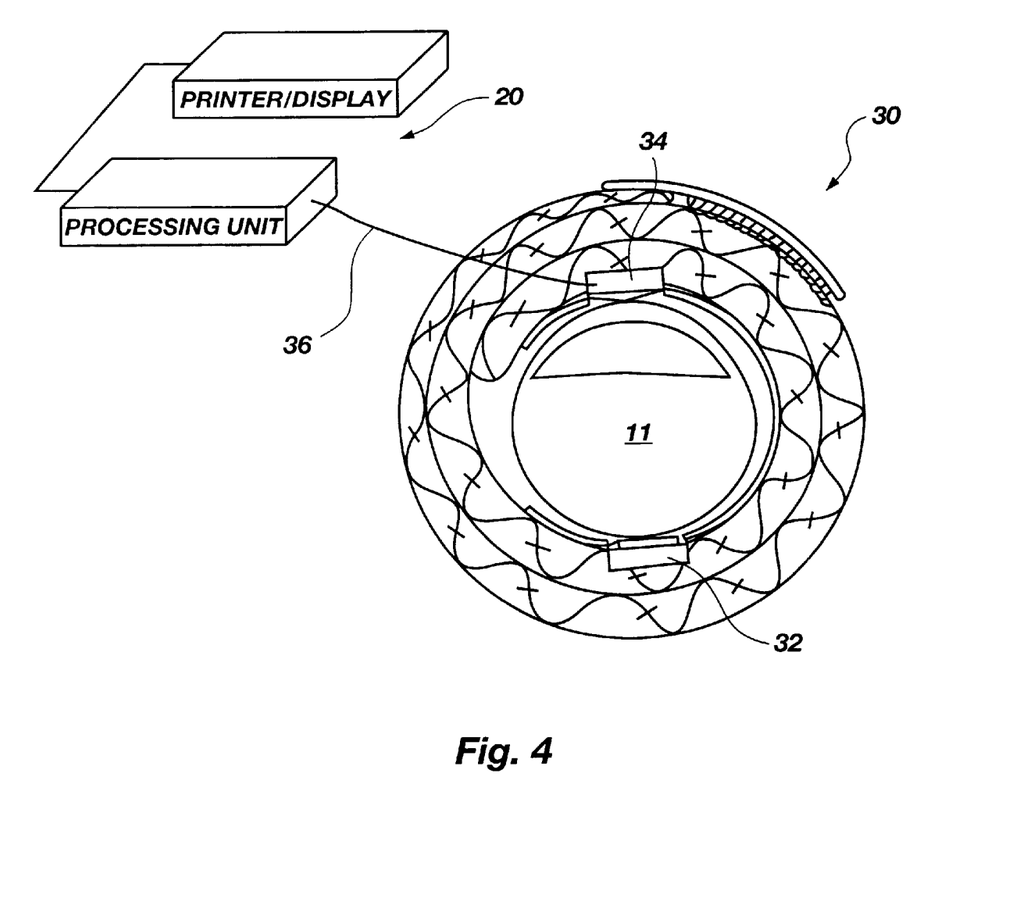
FIG. 4 is a schematic representation which illustrates a pulse oximetry sensor and associated monitor, which may be employed in association with the methods of the present invention.

Referring now to FIG. 4, blood oxygen measurements may be made by non-invasive means, such as by a pulse oximetry sensor 30 of a type known in the art, such as the OXYSNAP™ or Y-SENSOR™, both of which are manufactured by Novametrix. Pulse oximetry sensor 30 includes a two-frequency light emitting diode (LED) assembly 32 and a photodiode assembly 34 which are positionable on opposite sides of an appendage of the body of a patient, such as a finger 11, hand, toe, heel, foot, ear lobe, nose, or tongue. $SpO_2$ signals, which may be conveyed from pulse oximetry sensor 30 to computer 20, as known in the art, such as by a cable connector 36, are subsequently employed in the methods of the present invention.

Various other values that are employed in the methods of the present invention may be measured separately or assumed, then used in the methods, such as by entering these values into computer 20.

Preliminarily Determining Cardiac Output

Figure 2:
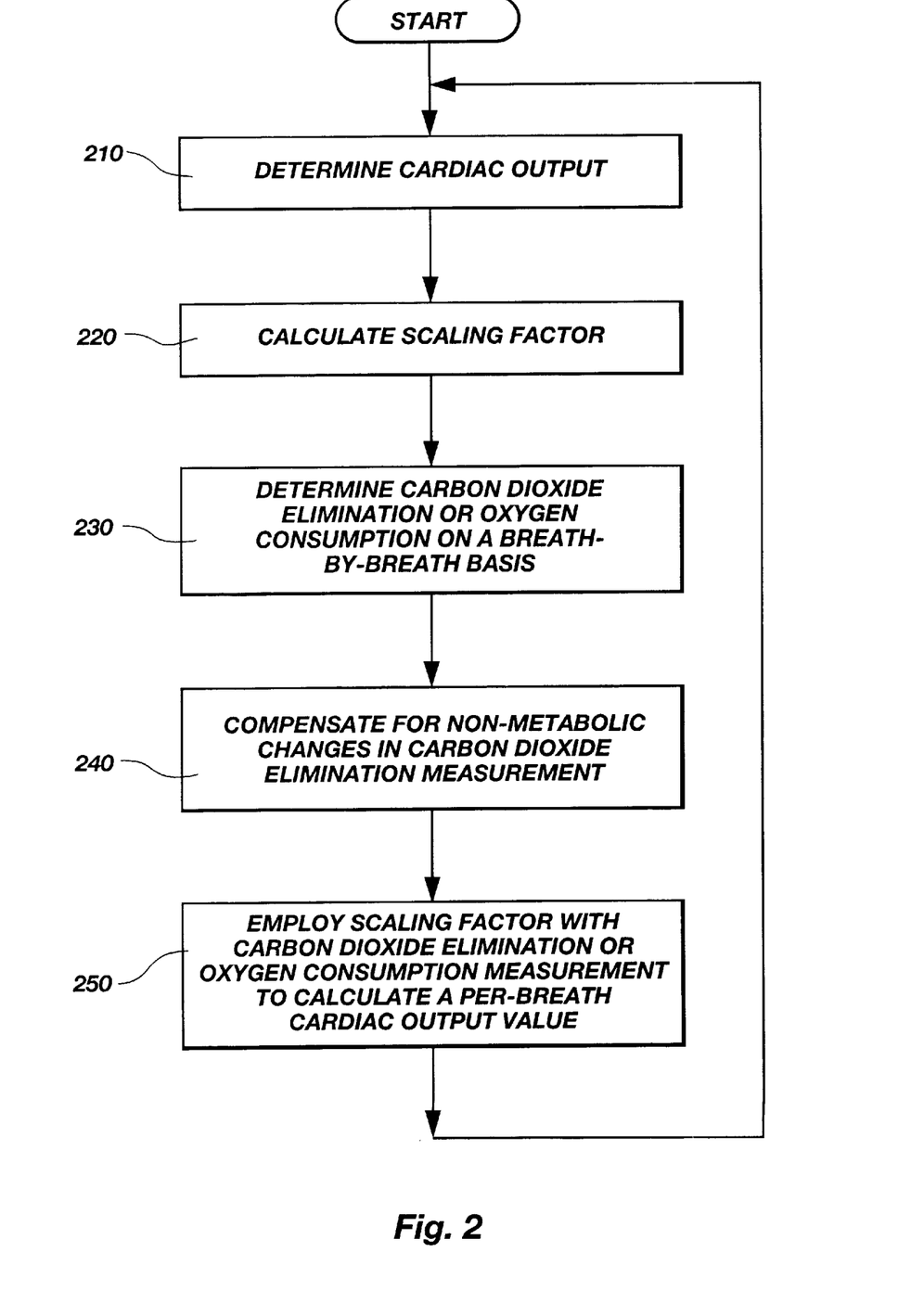
FIG. 2 is a flowchart that schematically illustrates the process of the present invention.

With reference to FIG. 2, the cardiac output of a patient is determined at 210. For each breathing cycle, the end-tidal partial pressure of $CO_2$ ($PetCO_2$ or $etCO_2$), carbon dioxide elimination ($VCO_2$), the fraction of inspired, or "mixed inspired", $CO_2$, and the airway deadspace are calculated, as known in the art. Carbon dioxide elimination is typically calculated as the integral of the respiratory flow over a breathing cycle (in milliliters) multiplied by fraction of $CO_2$ over the entire breath. The fraction of inspired $CO_2$ is the integral of $CO_2$ fraction times the air flow during inspiration (i.e., negative flow) divided by the volume (in milliliters) of inspired gas.

The values of $VCO_2$ and $PetCO_2$ may be filtered by employing a three-point or other median filter, which includes determining a median value from a group of the most recent $VCO_2$ and $PetCO_2$ values (e.g., the three most recent values in a three-point median filter) and sets the median of the most recent values as the most recent measured $VCO_2$ of $PetCO_2$ value, as known in the art.

Figure 5:
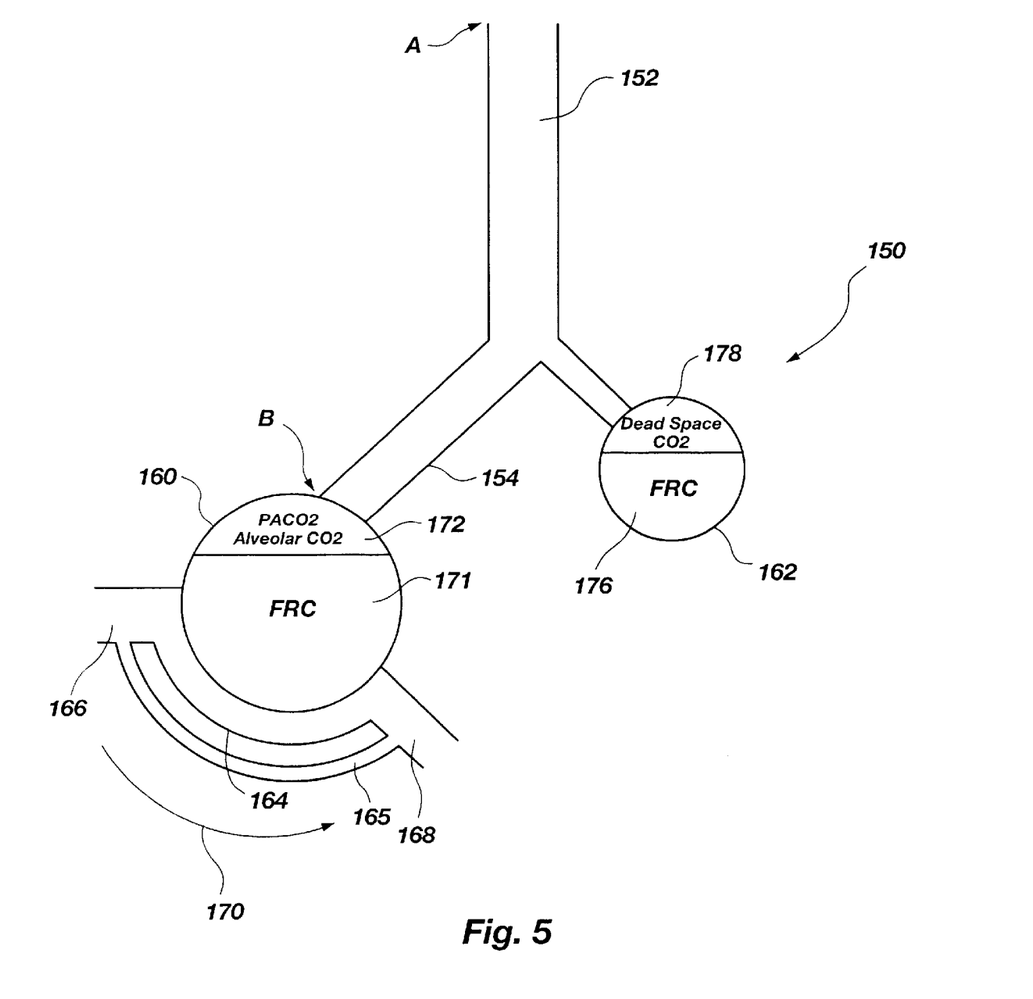
FIG. 5 is a schematic representation of the lungs of a patient.

Preferably, when calculating $VCO_2$, the $VCO_2$ value is corrected to account for anatomic deadspace and alveolar deadspace. With reference to FIG. 5, the lungs 150 of a patient may be described as including a trachea 152, two bronchi 154 and numerous alveoli 160, 162. The anatomic, or "serial", deadspace of lungs 150 includes the volume of the trachea 152, bronchi 154, and other components of lungs 150 which hold gases, but do not participate in gas exchange. The anatomic deadspace exists approximately in the region located between arrows A and B. The so-called shunted blood bypasses pulmonary capillaries by way of an intrapulmonary shunt 165.

Lungs 150 typically include alveoli 160 that are in contact with blood flow and which can facilitate oxygenation of the blood, which are referred to as "perfused" alveoli, as well as unperfused alveoli 162. Both perfused alveoli 160 and unperfused alveoli 162 may be ventilated. The volume of unperfused alveoli is the alveolar deadspace.

Perfused alveoli 160 are surrounded by and in contact with pulmonary capillaries 164. As deoxygenated blood 166 enters pulmonary capillaries 164, oxygen binds to the hemoglobin of the red blood cells of the blood, and $CO_2$ is released from the hemoglobin. Blood that exits pulmonary capillaries 164 in the direction of arrow 170 is referred to as oxygenated blood 168. In alveoli 160 and 162, a volume of gas known as the functional residual capacity (FRC) 171 remains following exhalation. The alveolar $CO_2$ is expired from a portion 172 of each of the alveoli 160 that is evacuated, or ventilated, during exhalation.

The ventilated portion 178 of each of the unperfused alveoli 162 may also include $CO_2$. The $CO_2$ of ventilated portion 178 of each of the unperfused alveoli 162, however, is not the result of $O_2$ and $CO_2$ exchange in that alveolus. Since the ventilated portion 178 of each of the unperfused alveoli 162 is ventilated in parallel with the perfused alveoli, ventilated portion 178 is typically referred to as "parallel"

deadspace (PDS). Unperfused alveoli 162 also include a FRC 176, which includes a volume of gas that is not evacuated during a breath.

In calculating the alveolar $CO_2$ partial pressure ($P_ACO_2$) of the patient, the FRC and the partial pressure of $CO_2$ in the parallel deadspace in each of the unperfused alveoli 162 is preferably accounted for. FRC may be estimated as a function of body weight and the airway deadspace volume by the following equation:

$$FRC = FRC\text{-}factor \cdot (airway\ deadspace + offset\ value),$$

where FRC-factor is either an experimentally determined value or is based on published data (e.g., "experiential" data) known in the art, and the offset value is a fixed constant which compensates for breathing masks or other equipment components that may add deadspace to the breathing circuit and thereby unacceptably skew the relationship between FRC and deadspace.

The partial pressure of $CO_2$ in the parallel deadspace $PCO_{2\ PDS}$) may be calculated from the mixed inspired $CO_2$ ($Vi_{CO_2}$) added to the product of the serial deadspace multiplied by the end tidal $CO_2$ partial pressure of the previous breath ($PetCO_2(n-1)$). Because the average partial pressure of $CO_2$ in the parallel deadspace is equal to the partial pressure of $CO_2$ in the parallel deadspace divided by the tidal volume ($V_t$)(i.e., the total volume of one respiratory cycle, or breath), the $CO_2$ partial pressure in the parallel deadspace may be calculated on a breath-by-breath basis, as follows:

$$PCO_{2\ PDS}(n) = [FRC/(FRC+V_t)] \cdot PCO_{2\ PDS}(n-1) + (P_{bar} \cdot (([ViCO_2 + deadspace \cdot (PetCO_2(n-1)/P_{bar})]/V_t) \cdot (V_t/(V_t+FRC))),$$

where (n) indicates a respiratory profile parameter (in this case, the partial pressure of $CO_2$ in the parallel deadspace) from the most recent breath and (n−1) indicates a respiratory profile parameter from the previous breath.

The end-tidal $CO_2$ partial pressure, which is assumed to be substantially equal to a weighted average of the partial pressure of $CO_2$ in all of the perfused and unperfused alveoli of a patient, may then be calculated as follows:

$$PetCO_2 = (r \cdot P_ACO_2) + (1-r)PCO_{2\ PDS},$$

where r is the perfusion ratio, which is calculated as the ratio of perfused alveolar ventilation to the total alveolar ventilation, or $(V_A - V_{PDS})/V_A$. The perfusion ratio may be assumed to be about 0.95 or estimated, as known in the art.

By rearranging the previous equation, the alveolar $CO_2$ partial pressure of the patient may be calculated. Preferably, alveolar $CO_2$ partial pressure is calculated from the end-tidal $CO_2$ and the $CO_2$ in the parallel deadspace, as follows:

$$P_ACO_2 = [PetCO_2 - (1-r)PCO_{2\ PDS}(n)]/r.$$

The alveolar $CO_2$ partial pressure may then be converted to $CO_2$ content using the following equation:

$$C_ACO_2 = (6.957 \cdot Hb_{conc} + 94.864) \cdot ln(1 + 0.1933(P_ACO_2)),$$

where $C_ACO_2$ is the content of $CO_2$ in the alveolar blood, measured in mmHg, and Hb is the concentration of hemoglobin in the blood of the pulmonary capillaries, measured in g/dl. In some instances, a hemoglobin count and, therefore, the hemoglobin concentration, are available and may be employed in calculating the $CO_2$ content. If a hemoglobin count or concentration is not available, another value (e.g., 11.0 g/dl) that is based upon experiential or otherwise known data may be employed in calculating the alveolar $CO_2$ content. Other equations for calculating the alveolar $CO_2$ content may also be employed in the method of the present invention.

In calculating $VCO_2$, the FRC and alveolar deadspace of the lungs of a patient may be accounted for by multiplying the FRC by the change in end-tidal partial pressure, such as by the following equation:

$$VCO_{2\ corrected} = VCO_2 + FRC \cdot \Delta PetCO_2/P_{bar},$$

where $\Delta PetCO_2$ is the breath-to-breath change in $PetCO_2$, $P_{bar}$ is barometric pressure and may be measured or assumed to equal to 101.33 kPa.

Baseline $PetCO_2$ and $VCO_2$ values, which are also referred to as "before re-breathing $PetCO_2$" and "before re-breathing $VCO_2$", respectively, occur during normal breathing and may be calculated as the average of a group of samples before the re-breathing process (e.g., the average of about all samples between 27 and 0 seconds before the start of a known re-breathing process). A $VCO_2$ value, which is typically referred to as "during re-breathing $VCO_2$", is calculated during the re-breathing process. "During re-breathing $VCO_2$" may be calculated as the average $VCO_2$ during the interval of 25 to 50 seconds into the re-breathing period.

The partial pressure of $CO_2$ in the alveolar blood during the re-breathing process may then be calculated by employing a regression line, which facilitates prediction of the stable, or unchanging, partial pressure of alveolar $CO_2$. Preferably, $P_ACO_2$ is plotted against the breath-to-breath change in partial pressure of $CO_2$ ($\Delta P_ACO_2$). A graph line that is defined by the plotted points is regressed, and the intersection between $P_ACO_2$ and zero $\Delta P_ACO_2$ is the predicted stable partial pressure of alveolar $CO_2$.

Pulmonary capillary blood flow may then be calculated as follows:

$$Q_{pcbf} = \frac{\left[\text{before re-breathing } V_{CO_2} - \text{during re-breathing } V_{CO_2}\right]}{\left[\text{during re-breathing } C_ACO_2 - \text{before re-breathing } C_ACO_2\right]}$$

Estimating Shunt Fraction

After a $Q_{pcbf}$ value has been determined by non-invasive means, the intrapulmonary shunt fraction of the cardiac output of the patient may be estimated. A shunt-estimating technique that is useful with the method of the present invention includes non-invasively determining the difference between the oxygen content of the end capillary blood and the oxygen content of the arterial blood of the patient, dividing the difference by the carbon dioxide elimination of the patient, and multiplying the difference by the patient's cardiac output ($Q_t$) and by the patient's respiratory quotient (RQ).

The shunt fraction ($Q_s/Q_t$) of the patient's cardiac output may be derived from various respiratory profile parameters, many of which may also be measured by non-invasive techniques. $Q_s/Q_t$ may be estimated in accordance with the following equation:

$$Q_s/Q_t = \frac{Cc'O_2 - CaO_2}{Cc'O_2 - CvO_2},$$

where $Cc'O_2$ is the oxygen content of the patient's end-capillary blood, $CaO_2$ is the oxygen content of the patient's arterial blood, and $CvO_2$ is the oxygen content of the patient's mixed venous blood. The denominator of the preceding equation ($Cc'O_2-CvO_2$) can be derived from the oxygen Fick equation that has been conventionally employed in re-breathing techniques for determining cardiac output:

$$Q_{pcbf} = \frac{V_{O_2}}{Cc'O_2 - CvO_2}.$$

This equation may be rewritten as:

$$Cc'O_2-CvO_2=VO_2/Q_{pcbf}$$

Moreover, since the respiratory quotient (RQ) is the ratio of the carbon dioxide elimination ($VCO_2$) to the oxygen uptake ($VO_2$) of a patient, as defined by the following equation:

$$RQ=VCO_2/VO_2,$$

and because of the difficulty of accurately measuring $VO_2$, especially in patients who require an elevated fraction of inspired oxygen, and the accuracy with which RQ can be assumed (typically about 0.7 to 1.0, and more particularly about 0.8 to 0.9 or 0.86), $VCO_2/RQ$ may be substituted for $VO_2$. Thus, $$Cc'O_2-CvO_2=VCO_2/(Q_{pcbf}RQ).$$

Accordingly, the shunt fraction, $Q_s/Q_t$, may be estimated by the following equation:

$$Q_s/Q_t = \frac{Cc'O_2 - CaO_2}{\frac{V_{CO_2}}{Q_{pcbf} \cdot RQ}}.$$

$VCO_2$, which was determined above in the determination of the pulmonary capillary blood flow of the patient, is the $CO_2$ production of the patient.

Alternatively, $VO_2$ may be measured as known in the art, and RQ can be calculated, rather than assumed. As another alternative, the $VO_2$ measurement may be divided by $Q_{pcbf}$ to directly determine $Cc'O_2-CvO_2$, in which case the following equation may be employed to estimate the shunt fraction:

$$Q_s/Q_t = \frac{Cc'O_2 - CaO_2}{\frac{V_{O_2}}{Q_{pcbf}}}.$$

The end-capillary oxygen content, $Cc'O_2$, may be calculated by the following equation:

$$Cc'O_2=(P_AO_2\cdot\alpha)+(Sc'O_2\cdot Hb_{capacity}\cdot Hb_{conc}).$$

The end-capillary oxygen content, $Cc'O_2$, may be calculated by the following equation:

$$Cc'O_2=(P_AO_2\cdot\alpha)+(Sc'O_2\cdot Hb_{capacity}\cdot Hb_{conc}),$$

where the alveolar oxygen tension of the patient may be calculated by the following formula:

$$P_AO_2=(FiO_2\cdot(P_{bar}-P_{H_2O}))-PaCO_2RQ\cdot(l-(FiO_2\cdot(l-RQ)))),$$

where $P_{bar}$ is the barometric pressure, $P_{H_2O}$ is the saturated water vapor pressure of a sample at ambient temperature and $PaCO_2$ is the partial pressure of $CO_2$ in the patient's arterial blood, which may be assumed, calculated, as known in the art from non-invasively obtained arterial blood gas data, or obtained by direct measurement. The blood oxygen solubility coefficient ($\alpha$), the end-capillary blood saturation ($Sc'O_2$), hemoglobin concentration ($Hb_{conc}$), and hemoglobin capacity ($Hb_{capacity}$) values may each be assumed values or determined by known techniques.

The oxygen content of the patient's arterial blood, $CaO_2$, may be calculated by the following equation:

$$CaO_2=(PaO_2\cdot\alpha)+(SaO_2\cdot Hb_{capacity}\cdot Hb_{conc}).$$

Since $PaO_2$ is a function of $SaO_2$, which is approximated by measuring $SpO_2$, the partial pressure of oxygen in the patient's arterial blood, $PaO_2$, may be calculated from the oxygen saturation ($SaO_2$) of the patient's arterial blood by employing an invertable version of a blood oxygen tension-saturation curve. Arterial blood oxygen saturation is determined non-invasively by known techniques, such as by pulse oximetry ($SpO_2$), as discussed previously in reference to FIG. 3.

Due to the inaccuracy of pulse oximetry measurements, which are typically in the range of about 2–3% and fairly consistent for a specific pulse oximeter, as well as the steepness of the tension-saturation curve between blood oxygen saturations of about 95–100%, a correction factor is employed in determining the oxygen saturation and partial pressure of oxygen in the arterial blood.

The correction factor may be an assumed value (e.g., ±2–3%) based on experiential error of a known degree when a specific type of pulse oximeter or a particular model of pulse oximeter of a particular manufacturer is employed to measure $SpO_2$. Alternatively, the correction factor may be determined by comparing a direct $SaO_2$ measurement from blood gas chemical analysis with an $SpO_2$ measurement taken by a pulse oximeter.

The correction factor may then be employed in combination with subsequent pulse oximetry measurements to more accurately determine the partial pressure of oxygen in the patient's arterial blood. This may be done by adding a correction factor to the $SpO_2$ measurement, by generating an equation to convert the $SPO_2$ measurement to a more accurate value, or by generating a special function in which the non-invasively measured, possibly somewhat inaccurate, $SpO_2$ measurement is employed to accurately determine $SaO_2$ or $PaO_2$.

When pulmonary capillary blood flow has been non-invasively determined and the shunt fraction estimated, the patient's cardiac output ($Q_t$) may be determined.

Calculating Cardiac Output

The cardiac output of the patient may then be corrected by adding the non-invasively measured volumetric rate of car diac output ($Q_t$) and the volumetric rate of flow of the patient's shunted blood (Q) by the following equation:

$$Q_t = Q_{pcbf} + Q_s.$$

Other, known methods of determining or estimating the intrapulmonary shunt of the patient may also be employed in intermittently determining the cardiac output of the patient.

Alternative Methods of Intermittently Measuring Cardiac Output

Alternatively, at reference 210 of FIG. 2, the cardiac output of a patient may be intermittently determined in accordance with the method of the present invention by other non-invasive techniques, such as other total or partial re-breathing methods or other differential Fick methods (e.g., adjusting the respiratory rate, inspiratory time, expiratory time, tidal volume, or adding a quantity of carbon dioxide to effect a change in $PetCO_2$ or $VCO_2$ in response to a change in ventilation) or invasive techniques, such as indicator dilution methods (e.g., thermodilution), or by other methods of determining cardiac output.

Calculating A Scaling Value to Be Employed in Determining Cardiac Output

The method of the present invention also includes calculating a scaling factor, at reference 220 of FIG. 2, that may be employed in determining the cardiac output of a patient on the basis of one or more respiratory profile parameters that may be measured non-invasively on a breath-by-breath basis. Once the cardiac output of the patient has been accurately determined, the scaling factor may be calculated by dividing the measured respiratory profile parameter by the cardiac output.

Preferably, the scaling factor is based on a respiratory or blood profile parameter that remains substantially constant between intermittent measurements of cardiac output and while the breathing or ventilation of a patient is stable. One such parameter is the arterial-venous carbon dioxide gradient, which is the denominator of the carbon dioxide Fick equation. Due to the presence of carbon dioxide stores in the blood and other tissues of the patient, the $CO_2$ content of the venous blood of the patient remains substantially constant over short time periods, even during re-breathing. Accordingly, the arterial-venous carbon dioxide gradient typically remains substantially constant over the period of the time constant associated with the patient's carbon dioxide stores. As the arterial-venous gradient ($CvCO_2-CaCO_2$) remains substantially constant during stable breathing or ventilation and without a substantial change in the carbon dioxide stores, since $VCO_2$ may be relatively easily and accurately measured, and since $VCO_2$ is a relatively good indicator of cardiac output, a preferred embodiment of the method of the present invention includes calculating cardiac output on the basis of the carbon dioxide Fick equation:

$$Q_t = VCO_2/(CvCO_2 - CaCO_2),$$

where $CvCO_2$ is the content of $CO_2$ in the venous blood of the patient and $CaCO_2$ is the content of $CO_2$ in the arterial blood of the patient. Accordingly, the scaling factor of the present embodiment is preferably a modification of the arterial-venous carbon dioxide gradient value, which is referred to as an AV gradient, and which includes any deadspace, shunt, or other corrections that were made in the intermittent determination of cardiac output.

Alternatively, the scaling factor may be based on a portion of the arterial-venous gradient, such as on the content of carbon dioxide or oxygen in the venous blood or the content of carbon dioxide or oxygen in the arterial blood, assuming that the value upon which the scaling factor is based remains substantially constant between intermittent measurements of cardiac output and while the breathing or ventilation of the patient is substantially stable.

In a second embodiment of the method, wherein $VCO_2$ is non-invasively measured to calculate cardiac output, the oxygen Fick equation, modified to replace $VO_2$ with $VCO_2$, is employed:

$$Q_t = \frac{V_{CO_2}}{K \cdot RQ \cdot (Cc'O_2 - CvO_2) + S},$$

where $Cc'O_2$ and $CvO_2$ may each be determined on the basis of continuous measurements and K is the constant value. The scaling factor, K, compensates for any deadspace, shunt, or other corrections that were made in the intermittent determination of cardiac output. If no such corrections were made, K is substantially equal to one. RQ may either be measured or assumed to be a constant value, as discussed previously. An offset constant, S, may also be employed to compensate for deadspace, shunt, or other factors that substantially constantly affect the non-invasively, continuously measured cardiac output value.

In alternative embodiments of the present invention, other variations of the Fick principle may be employed to determine cardiac output in accordance with the method of the present invention. An exemplary variation of the Fick principle, represented by the following equation:

$$Q_t = VCO_2/(13.4 \cdot K \cdot RQ \cdot (SaO_2 - SvO_2)),$$

where $SaO_2$ and $SvO_2$ are the oxygen saturations of arterial and venous blood, respectively, is disclosed in U.S. Pat. No. 4,949,724, which issued to Mahutte et al. on Aug. 21, 1990, the disclosure of which is hereby incorporated by reference in its entirety. In another exemplary variation of the Fick principle, the difference in partial pressures of arterial and venous blood gases (i.e., either $O_2$ or $CO_2$) may be employed to determine the cardiac output of a patient. These variations of the denominator of the carbon dioxide Fick equation, as well as others known in the art, may be assumed to remain substantially constant during stable breathing or ventilation. Alternatively, one or more of the parameters of these variations of the denominator of the carbon dioxide Fick equation may be continuously measured and modified by a constant value in order to facilitate the accurate estimation of cardiac output. As in the first embodiment, due to the presence of carbon dioxide stores in the blood and other tissues of a patient, the partial pressures and saturations of blood gases remain substantially constant during stable respiration or ventilation and while the carbon dioxide stores remain substantially unchanged.

An offset constant may also be employed to modify the cardiac output value obtained with the scaling factor. The offset constant may compensate for any deadspace, shunt, or other factors that substantially constantly affect the non-invasively, continuously measured cardiac output value. For example, a cardiac output value obtained with a scaling factor may be further modified by adding an offset constant thereto or subtracting an offset constant therefrom.

Alternatively, scaling factors and offset constants may be employed with the oxygen consumption ($VO_2$) of the patient to facilitate the continuous, non-invasive measurement of the cardiac output or pulmonary capillary blood flow of the patient.

Breath-By-Breath Determination of Cardiac Output

Once the scaling factor has been determined, breath-by-breath measurements of $VCO_2$, obtained at reference 230 of FIG. 2, may be employed with the scaling factor, at reference 250 of FIG. 2, to determine the cardiac output of a patient. $VCO_2$ may be continuously measured with $CO_2$ and flow sensors and monitors, as described above in reference to FIG. 3.

In accordance with the first embodiment of the inventive method, the $VCO_2$ measurement is divided by the arterial venous gradient carbon dioxide constant to determine the cardiac output of the patient. Accordingly, the cardiac output of the patient may be determined with each breath. Alternatively, $VCO_2$ may be filtered over a particular time period or a particular number of breaths, and cardiac output determined on a per breath basis. These calculations may be performed manually or by computer 20.

In the second embodiment of the present invention, a $VCO_2$ measurement is divided by the product of the respiratory quotient, K, and the difference between $Cc'O_2$ and $CvO_2$ to determine the cardiac output of the patient. Since the patient's end-tidal partial pressure of oxygen ($PetO_2$) and the partial pressure of oxygen in the patient's arterial blood (PaO) may both be measured continuously, $Cc'O_2$ and $CvO_2$ may be continuously determined, as previously discussed. The $VCO_2$ measurement may be determined with each breath, as an average of a particular number of breaths, or as an average over a particular period of time.

Determining Cardiac Output During or Following Changes in Ventilation

In stable patients, the amount of $CO_2$ eliminated per breath is typically about equal to the amount of metabolically produced $CO_2$ per breath. If the breathing or ventilation of the patient changes during breath-by-breath monitoring of cardiac output, however, the $VCO_2$ measurement will typically change until after steady state breathing has been restored and the transient effect has diminished, typically at least 5 to 30 minutes after the onset of a change in ventilation or breathing, such as hyperventilation. Accordingly, in order to accurately determine the cardiac output of a patient during or following a change in ventilation or breathing, it is preferable to compensate for any variation in the $VCO_2$ measurement, at reference 240 of FIG. 2.

In each of the first and second embodiments of the method of the present invention, a compensatory signal, or correction factor, may be generated to compensate for variation in the $VCO_2$ measurement or any other respiratory or blood gas profile parameters that are employed in determining the cardiac output of the patient and which may be non-metabolically altered during or after a change in ventilation or breathing.

Preferably, a change in the ventilation of a patient is first detected by monitoring either $VCO_2$ or $PetCO_2$, as discussed in reference to FIG. 2. A substantial change (e.g., at least 5, 10, or 20%) in $VCO_2$ or $PetCO_2$, relative to a per breath $VCO_2$ or $PetCO_2$ measurement taken before the change in ventilation or breathing, may be considered as a change in the ventilation of the patient.

Once a change in ventilation has been detected, a compensatory signal, or correction factor, is generated in order to compensate for the non-metabolic change and, thus, provide for a more accurate cardiac output estimate. The compensatory signal may be generated based on a variety of factors, including, without limitation, the amount of time that has elapsed since the onset of a change in ventilation or breathing, the type of change in ventilation or breathing, the condition of the patient's lungs, and the magnitude of change in the measured carbon dioxide elimination relative to the stable, or "normal" carbon dioxide elimination, as measured or estimated prior to the change in ventilation or breathing. Since a non-metabolic change in the carbon dioxide elimination measurement that is caused by a change in ventilation or breathing gradually diminishes over time, the compensatory signal is preferably adjusted over time in a similar manner. Adjusting the compensatory signal in this manner facilitates the continued, substantially accurate estimation of cardiac output while or after the patient's ventilation or breathing has changed.

An exemplary compensatory signal may be generated by employing a time constant that may be based upon a model of the duration of a particular cause of a change in ventilation or breathing (e.g., hyperventilation). Preferably, the amount of time that has elapsed since the onset of the change in ventilation or breathing and the magnitude of the non-metabolic change in one or more respiratory or blood gas profile parameters are considered in generating the compensatory signal.

If a sudden, or step, change in the monitored signal is observed, the amount of the change is assumed to be caused by the non-metabolic change in ventilation. The compensating signal may be an exponentially decreasing signal with an initial magnitude proportional to the size of the step change and decreasing by a fixed percentage with each subsequent breath. For example, if the step change was an increase in $VCO_2$ from about 200 to about 300 ml per minute, a compensating signal may have an initial value of 100 and may be reduced by 3%, compounded, for each subsequent breath (i.e., 100, 97, 94, 91, etc.). This compensatory signal would be subtracted from the measured $VCO_2$ value for each breath until the compensatory signal reaches zero, thus maintaining a $VCO_2$ signal that reflects the metabolic level of about 200 ml of $CO_2$ eliminated per minute, preferably until the non-metabolic change corrects itself.

One or more of the respiratory or blood gas profile parameters (e.g., $VCO_2$, $VO_2$ or AV gradient) is modified by the compensatory signal to facilitate the accurate estimation of cardiac output on a breath-by-breath basis. Either non-metabolically altered or unaltered parameters may be modified.

As an example of the modification of a respiratory or blood gas profile parameter, the arterial-venous carbon dioxide gradient may be modified by the compensatory signal in order to facilitate the accurate breath-by-breath determination of the cardiac output of the patient.

As an example of a variation of the method of modifying a respiratory or blood gas profile parameter, the scaling factor (K) or another component of the cardiac output formula employed may be modified by the compensatory signal to facilitate the accurate breath-by-breath determination of the cardiac output of the patient.

Repetition of Intermittent Cardiac Output Measurement

Due to the potential for changes in the arterial-venous carbon dioxide gradient or equivalent measurements over time, especially as the carbon dioxide stores in the blood or other tissues of the patient change, the cardiac output of the patient is preferably updated periodically or as needed, at reference 210 of FIG. 2. Such updating may maintain the accuracy of cardiac output measurements taken on a breath-by-breath basis. Cardiac output may be updated by repeating the intermittent measurement, as discussed above.

The frequency with which intermittent cardiac output measurements may be made is preferably determined, as known in the art, by estimating the size of the patient's carbon dioxide stores from the patient's deadspace measurement, which may be made, as discussed above. From this estimation of the size of the patient's carbon dioxide stores, the amount of time the carbon dioxide stores will remain, which is referred to as the "time constant" of the carbon dioxide stores, may be determined as known in the art. The length of time the arterial-venous carbon dioxide gradient of the patient's blood or any equivalent measurements will remain substantially non-metabolic may be similarly determined. Preferably, the cardiac output of the patient is re-measured by the intermittent technique within the time constant, or while the arterial-venous gradient remains substantially constant.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method of substantially continuously determining a pulmonary capillary blood flow of a patient, comprising:
   determining an intermittent pulmonary capillary blood flow using a selected method of determining pulmonary capillary blood flow;
   measuring a carbon dioxide elimination of the patient;
   obtaining a scaling factor with said intermittent pulmonary capillary blood flow and said carbon dioxide elimination; and
   modifying a subsequent carbon dioxide elimination of the patient by a scaling value comprising said scaling factor to calculate a pulmonary capillary blood flow value.

2. The method of claim 1, wherein said determining comprises conducting an indicator dilution technique.

3. The method of claim 2, further comprising intermittently repeating said indicator dilution technique at least once.

4. The method of claim 1, wherein said obtaining comprises:
   measuring a carbon dioxide content of venous blood of the patient; and
   measuring a carbon dioxide content of arterial blood of the patient.

5. The method of claim 1, wherein said obtaining comprises:
   measuring an oxygen saturation of arterial blood of the patient; and
   measuring an oxygen saturation of venous blood of the patient.

6. The method of claim 1, wherein said obtaining comprises:
   measuring an end capillary oxygen content of the patient; and
   measuring an oxygen content of arterial blood of the patient.

7. The method of claim 1, wherein said obtaining comprises:
   measuring a partial pressure of an arterial blood gas; and
   measuring a partial pressure of a venous blood gas.

8. The method of claim 1, wherein said determining comprises conducting a differential Fick cardiac output measurement technique.

9. The method of claim 1, wherein said determining comprises partial or total re-breathing.

10. The method of claim 1, wherein said determining comprises adjusting a respiratory rate.

11. The method of claim 1, wherein said determining comprises adjusting a period of inspiration or expiration.

12. The method of claim 1, wherein said determining comprises adjusting a tidal volume.

13. The method of claim 1, wherein said determining pulmonary capillary blood flow comprises adding a volume of carbon dioxide to ventilation of the patient.

14. The method of claim 8, further comprising intermittently repeating said determining at least once.

15. The method of claim 1, wherein said measuring comprises measuring a per-breath volume of exhaled carbon dioxide.

16. The method of claim 1, further comprising intermittently determining said scaling factor.

17. The method of claim 1, further comprising updating said scaling factor.

18. The method of claim 1, further comprising compensating for a non-metabolic change in said carbon dioxide elimination.

19. The method of claim 18, wherein said compensating comprises detecting said non-metabolic change.

20. The method of claim 18, wherein said compensating comprises generating a compensatory signal in response to said non-metabolic change.

21. The method of claim 20, wherein said compensatory signal is based on a magnitude of said non-metabolic change.

22. The method of claim 20, wherein said compensatory signal is based on an amount of time elapsed since the onset of said non-metabolic change.

23. The method of claim 20, further comprising modifying at least one of said carbon dioxide elimination and said scaling value by said compensatory signal.

24. The method of claim 1, wherein said scaling factor comprises an entire scaling value.

25. The method of claim 1, wherein said scaling factor comprises a portion of said scaling value.

26. The method of claim 1, wherein said obtaining comprises dividing said intermittent pulmonary capillary blood flow by said carbon dioxide elimination.

27. The method of claim 26, wherein said modifying comprises dividing said subsequent carbon dioxide elimination by said scaling value.

28. The method of claim 1, further comprising modifying said pulmonary capillary blood flow value by an offset constant.

29. A method of substantially continuously, non-invasively determining a cardiac output of a patient, comprising:
   obtaining a scaling value comprising a scaling factor;
   non-invasively measuring a carbon dioxide elimination of the patient;
   compensating for a non-metabolic change in at least one of said carbon dioxide elimination and said scaling value; and
   calculating the cardiac output by dividing said carbon dioxide elimination by said scaling value.

30. The method of claim 29, further comprising detecting said non-metabolic change.

31. The method of claim 29, wherein said compensating comprises modifying at least one of said carbon dioxide elimination and said scaling value.

32. The method of claim 31, wherein said scaling value comprises an arterial-venous gradient of the patient.

33. The method of claim 29, wherein an entire said scaling value comprises said scaling factor.

34. The method of claim 29, wherein said scaling factor comprises at least a portion of said scaling value.

35. The method of claim 29, wherein said calculating comprises modifying the cardiac output by an offset constant.

36. A method of non-invasively measuring cardiac output of a patient on a breath-by-breath basis, comprising:

measuring a per breath volume of carbon dioxide exhaled by the patient;

measuring an arterial-venous gradient of the patient; and compensating for a non-metabolic change in at least one of said per breath volume of carbon dioxide and said arterial-venous gradient.

37. The method of claim 36, further comprising detecting said non-metabolic change.

38. The method of claim 36, wherein said compensating comprises generating a compensatory signal in response to said non-metabolic change.

39. The method of claim 38, wherein said compensatory signal is based on a magnitude of said non-metabolic change.

40. The method of claim 38, wherein said compensatory signal is based on an amount of time elapsed since the onset of said non-metabolic change.

41. The method of claim 38, further comprising modifying at least one of said per breath volume of carbon dioxide and said arterial-venous gradient by said compensatory signal.

42. A method of substantially continuously determining a cardiac output of a patient, comprising:

determining an intermittent cardiac output using a selected method of determining cardiac output;

non-invasively measuring a carbon dioxide elimination of the patient;

obtaining a scaling factor with said intermittent cardiac output and said carbon dioxide elimination; and modifying another carbon dioxide elimination with a scaling value comprising said scaling factor to calculate a cardiac output value.

43. The method of claim 42, wherein said obtaining comprises dividing said intermittent cardiac output by said carbon dioxide elimination.

44. The method of claim 43, wherein said modifying comprises multiplying said another carbon dioxide elimination by said scaling value.

45. The method of claim 42, further comprising modifying said cardiac output value by an offset constant.

46. The method of claim 45, wherein said modifying comprises adding said offset constant to or subtracting said offset constant from said cardiac output value.

47. A method of substantially continuously determining a cardiac output of a patient, comprising:

determining an intermittent cardiac output using a selected method of determining cardiac output;

measuring an oxygen consumption of the patient;

obtaining a scaling factor with said intermittent cardiac output and said oxygen consumption; and calculating a cardiac output value with another oxygen consumption and a scaling value comprising said scaling factor.

48. The method of claim 47, wherein said obtaining comprises dividing said intermittent cardiac output by said oxygen consumption.

49. The method of claim 48, wherein said calculating comprises multiplying said another oxygen consumption by said scaling value.

50. The method of claim 47, wherein said calculating further comprises modifying said cardiac output value by an offset constant.

51. The method of claim 50, wherein said modifying comprise adding said offset constant to or subtracting said offset constant from said cardiac output value.

52. A method of substantially continuously determining a pulmonary capillary blood flow of a patient, comprising:

determining an intermittent pulmonary capillary blood flow using a selected method of determining pulmonary capillary blood flow;

measuring an oxygen consumption of the patient;

obtaining a scaling factor with said intermittent pulmonary capillary blood flow and said oxygen consumption; and calculating a pulmonary capillary blood flow value with at least one subsequent oxygen consumption measurement and a scaling value comprising said scaling factor to calculate pulmonary capillary blood flow.

53. The method of claim 52, wherein said obtaining comprises dividing said intermittent pulmonary capillary blood flow by said oxygen consumption.

54. The method of claim 53, wherein said calculating comprises multiplying said oxygen consumption value by said scaling value.

55. The method of claim 52, wherein said calculating further comprises modifying said pulmonary capillary blood flow value by an offset constant.

56. The method of claim 55, wherein said modifying comprises adding said offset constant to or subtracting said offset constant from said pulmonary capillary blood flow value.

* * * * *

UNITED STATES PATENT AND TRADEMARK OFFICE
CERTIFICATE OF CORRECTION

PATENT NO. : 6,217,524 B1
DATED : April 17, 2001
INVENTOR(S) : Joseph A. Orr, Michael B. Jaffe, Kai Kück and Dinesh G. Haryadi It is certified that error appears in the above-identified patent and that said Letters Patent is hereby corrected as shown below:

Column 1,
Line 55, in the equation, change "$VO_2$" to -- $V_{O_2}$ --
Lines 57 and 65, change "$VO_2$" to -- $V_{O_2}$ --

Column 2,
Lines 6, 15 and 42, change "$VO_2$" to -- $V_{O_2}$ --
Lines 21, 22, 41 and 49, change "$VCO_2$" to -- $V_{CO_2}$ --
Line 26, change "$VCO_2$" to -- $V_{CO_2}$ -- and change "$VO_2$" to -- $V_{O_2}$ --
Line 29, in the equation, change "$VO_2$" to -- $V_{O_2}$ -- and change "$VCO_2$" to -- $V_{CO_2}$ --
Line 39, in the equation, change "$VCO_2$" to -- $V_{CO_2}$ --
Line 64, in the equation, change "$Q_1$" to -- $Q_t$ -- and change "$VCO_2$" to -- $V_{CO_2}$ --

Column 3,
Lines 15 and 61, change "$(PACO_2)$" to -- $(P_ACO_2)$ --

Column 4,
Line 4, change "$Q_1$" to -- $Q_t$ --
Line 9, change "$VCO_2$" to -- $V_{CO_2}$ --
Line 31, in the equation, change "$FECO_2$" to -- $F_ECO_2$ --
Lines 34 and 37, change "$FECO_2$" to -- $F_ECO_2$ --
Line 43, change "$CVCO_2$" to -- $CvCO_2$ --
Line 50, change "patient:," to -- patient, --

Column 6,
Line 64, change "$VCO_2$" to -- $V_{CO_2}$ --

Column 7,
Line 8, change "$(VO_2)$" to -- $(V_{O_2})$ --
Line 12, change "$(VCO_2)$" to -- $(V_{CO_2})$ --
Line 18, in the equation, change "$VCO_2$" to -- $VCO_2$ --

Column 8,
Line 18, change "$(VCO_2)$" to -- $(V_{CO_2})$ --
Lines 27, 30 and 33, change "$VCO_2$" to -- $V_{CO_2}$ --
Line 34, change "$VCO_2$" (both occurrences) to -- $V_{CO_2}$ --

UNITED STATES PATENT AND TRADEMARK OFFICE
CERTIFICATE OF CORRECTION

PATENT NO.    : 6,217,524 B1
DATED         : April 17, 2001
INVENTOR(S)   : Joseph A. Orr, Michael B. Jaffe, Kai Kück and Dinesh G. Haryadi It is certified that error appears in the above-identified patent and that said Letters Patent is hereby corrected as shown below:

Column 9,
Line 4, change "($P_ACO_2$)" to -- ($P_ACO_2$) --
Line 22, change "$PCO_2$" to -- ($PCO_2$ --
Line 34, in the equation, change "$(n^{-1})$" to -- (n-1) -- and change "$ViCO_2$" to -- $Vi_{CO2}$ --
Lines 47 and 59, in the equation change "$P_ACO_2$" to -- $P_ACO_2$ --
Line 65, in the equation, change "$C_ACO_2$" to -- $C_ACO_2$ -- and change "$P_ACO_2$" to -- $P_ACO_2$ --
Line 67, change "$C_ACO_2$" to -- $C_ACO_2$ --

Column 10,
Lines 8, 20, 22, 26 and 27, change "$VCO_2$" to -- $V_{CO2}$ --
Line 15 and 44, in the equation, change "$VCO_2$" (both occurrences) to -- $V_{CO2}$ --
Line 29, change "$VCO_2$" (both occurrences) to -- $V_{CO2}$ --
Line 36, change "$P_ACO_2$" to -- $P_ACO_2$ --
Line 37, change "$(\Delta P_ACO_2)$" to -- $(\Delta P_ACO_2)$ --
Line 39, change "$P_ACO_2$" to -- $P_ACO_2$ -- and change "$\Delta P_ACO_2$" to -- $\Delta P_ACO_2$ --
Line 45, in the equation change "$C_ACO_2$" (both occurrences) to -- $C_ACO_2$ --

Column 11,
Line 17, in the equation, change "$V_{O2}$" to -- $V_{O2}$ --
Line 23, in the equation, change "$VO_2$" to -- $V_{O2}$ --
Lines 27, 36 and 51, change "$VCO_2$" to -- $V_{CO2}$ --
Lines 27, 32, 37, 54 and 56 change "$VO_2$" to -- $V_{O2}$ --
Line 30, in the equation, change "$VCO_2$" to -- $V_{CO2}$ -- and change "$VO_2$" to -- $V_{O2}$ --
Line 40, in the equation, change "$VCO_2$" to -- $V_{CO2}$ --
Line 47, in the equation, change "$V_{CO2}$" to -- $VCO_2$ --
Line 62, in the equation, change "$V_{O2}$" to -- $V_{O2}$ --
Line 70, in the equation, change "$P_ACO_2$" to -- $P_ACO_2$ --
Lines 72-73, delete "The end-capillary oxygen content, Cc'O$_2$, may be calculated by the following equation:"

Column 12,
Line 3, delete "Cc'O$_2$=( $P_AO_2$·α)+(Sc'O$_2$·$Hb_{capacity}$·$Hb_{conc}$),"
Line 9, in the equation, change "$P_AO_2$" to -- $P_AO_2$ -- and change both occurrences of "*l*" to -- 1 --
Line 67, change "car" to -- car- --

UNITED STATES PATENT AND TRADEMARK OFFICE
CERTIFICATE OF CORRECTION

PATENT NO.    : 6,217,524 B1
DATED         : April 17, 2001
INVENTOR(S)   : Joseph A. Orr, Michael B. Jaffe, Kai Kück and Dinesh G. Haryadi It is certified that error appears in the above-identified patent and that said Letters Patent is hereby corrected as shown below:

Column 13,
Line 2, change "(Q)" to -- ($Q_s$) --
Lines 20, 53 and 54, change "$VCO_2$" to -- $V_{CO_2}$ --
Line 60, in the equation, change "$VCO_2$" to -- $V_{CO_2}$ --

Column 14,
Lines 7 and 64, change "$VCO_2$" to -- $V_{CO_2}$ --
Line 9, change "$VO_2$" to -- $V_{O_2}$ -- and change "$VCO_2$" to -- $V_{CO_2}$ --
Line 12, in the equation, change "$V_{CO_2}$" to -- $VCO_2$ --
Line 33, in the equation, change "$VCO_2$" to -- $V_{CO_2}$ --
Line 70, change "$VCO_2$" to -- $V_{CO_2}$ --

Column 15,
Lines 3, 7, 11, 16, 23, 34, 41, 46, 52, 54 and 55, "$VCO_2$" to -- $V_{CO_2}$ --
Line 21, change "(PaO)" to -- $PaO_2$) --
Line 32, change "$CO_2$per" to -- $CO_2$ per --

Column 16,
Lines 24, 28 and 30, change "$VCO_2$" to -- $V_{CO_2}$ --
Line 35, change "$VCO_2$" to -- $V_{CO_2}$ -- and change "$VO_2$" to -- $V_{O_2}$ --

Signed and Sealed this

Seventeenth Day of June, 2003

JAMES E. ROGAN
*Director of the United States Patent and Trademark Office*